United States Patent [19]

Manganaro

[11] 3,985,744

[45] Oct. 12, 1976

[54] PRODUCTION OF GRANULAR SODIUM DICHLOROISOCYANURATE

[75] Inventor: James L. Manganaro, Hightstown, N.J.

[73] Assignee: FMC Corporation, Philadelphia, Pa.

[22] Filed: Mar. 13, 1975

[21] Appl. No.: 558,092

Related U.S. Application Data

[63] Continuation-in-part of Ser. No. 342,511, March 19, 1973, Pat. No. 3,886,249.

[52] U.S. Cl. .................... 260/248 C

[51] Int. Cl.$^2$ .................... C07D 251/28

[58] Field of Search .................... 260/248 C

[56] References Cited

UNITED STATES PATENTS

| | | | |
|---|---|---|---|
| 2,828,308 | 3/1958 | Lorenz | 260/248 |
| 3,035,054 | 5/1962 | Symes et al. | 260/248 |
| 3,035,056 | 5/1962 | Symes | 260/248 |
| 3,035,057 | 5/1962 | Symes et al. | 260/248 |
| 3,072,654 | 1/1963 | Vazopolos | 260/248 |
| 3,094,525 | 6/1963 | Marek | 260/242 |
| 3,205,229 | 9/1965 | Matzner | 260/242 |
| 3,221,014 | 11/1965 | Symes | 260/248 |
| 3,289,312 | 12/1966 | Wenzke et al. | 260/248 X |
| 3,294,797 | 12/1966 | Shallenberger et al. | 260/248 |
| 3,522,254 | 7/1970 | Meshiah | 260/248 |
| 3,803,144 | 4/1974 | Berkowitz | 260/248 |
| 3,818,002 | 6/1974 | Goelz et al. | 260/248 |
| 3,818,004 | 6/1974 | Berkowitz | 260/248 |

*Primary Examiner*—John M. Ford

[57] ABSTRACT

Anhydrous sodium dichloroisocyanurate is obtained as a free flowing granular product of bulk density 0.84 to 0.94 g/cc by compacting, granulating and sizing sodium dichloroisocyanurate dihydrate to obtain a granular dihydrate product having at least 60% by weight of particles having a screen size of −10 +70 mesh (U.S. Standard) and then dehydrating said granular dihydrate product. The ability to produce anhydrous granular sodium dichloroisocyanurate of a bulk density 0.84 to 0.94 g/cc provides a means for controlling an important parameter in producing flowable non-segregating compositions, as for example, detergent compositions.

9 Claims, 1 Drawing Figure

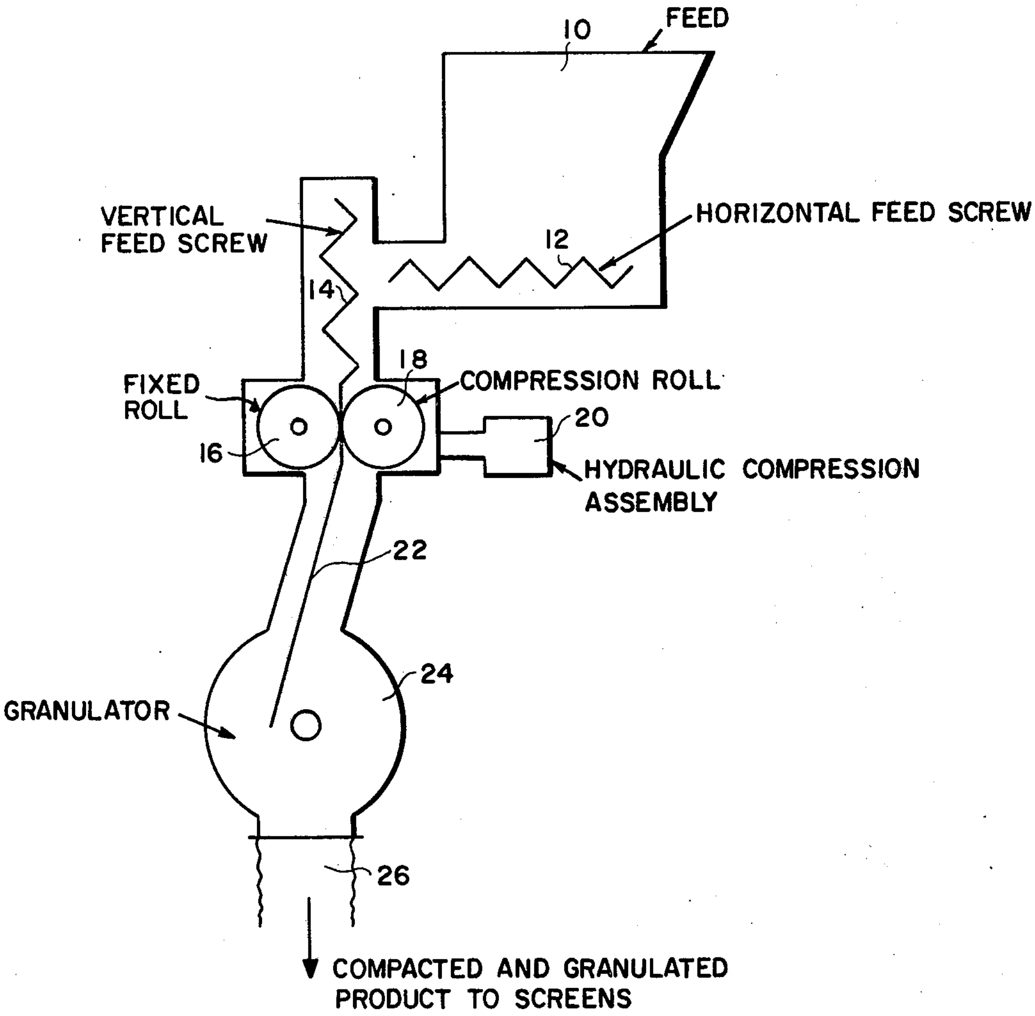
FEED
10
VERTICAL FEED SCREW
HORIZONTAL FEED SCREW
12
14
18
FIXED ROLL
COMPRESSION ROLL
20
16
HYDRAULIC COMPRESSION ASSEMBLY
22
24
GRANULATOR
26
COMPACTED AND GRANULATED PRODUCT TO SCREENS

PRODUCTION OF GRANULAR SODIUM DICHLOROISOCYANURATE

The application is a continuation-in-part of copending application Ser. No. 342,511, filed Mar. 19, 1973, now U.S. Pat. No. 3,886,249.

This invention relates to granular sodium dichloroisocyanurate, and more particularly, relates to granular anhydrous sodium dichloroisocyanurate of bulk density 0.84 to 0.94 g/cc and process for producing it.

Sodium dichloroisocyanurate is widely used as a source of available chlorine in solid bleach and detergent compositions, and in chlorination of water in swimming pools. It is desirably sold as granules (20 to 70 mesh — U.S. Standard Screen). Any significant deviation from this particle size range adversely affects the flowability of the product. Since sodium dichloroisocyanurate is generally recovered from manufacturing operations as a powder finer than 200 mesh, it is therefore necessary to pelletize the fine material to produce a free-flowing granular product. This may be done by high-pressure tableting, followed by crushing, or by sheeting in a roll compactor into corrugated, readily frangible sheets, which are then broken down to granules in any convenient machine.

Both processes have disadvantages. In tableting, anhydrous sodium dichloroisocyanurate sticks to the molds, so that it was considered necessary to add a mold lubricant. However, in accordance with Japanese Pat. No. 1967-23198, published Nov. 10, 1967, the adhesion of the powder to the mold can be overcome by first adding 4 to 14% of water to the anhydrous material. The resultant hydrate does not stick to the mold, even at the required pressure of 1,000 kilograms per square centimeter (equivalent to about 14,200 pounds per square inch).

In the sheeting or compaction process, other problems arise. A principal problem is that of excessive fines production, requiring recycle rates of 60 to 80%, where a +70 mesh granule is desired. A second problem is that temperature control is essential in the process, since anhydrous sodium dichloroisocyanurate is known to undergo heat-induced decomposition. In order to prevent such decomposition, which can result in actual fires, careful monitoring of the process is required. Additionally, it is essential to avoid contamination of the product with organics such as lubricating oil, since this can cause thermal decomposition of the product.

Granular sodium dichloroisocyanurate produced by these methods has a narrow range of bulk densities of from about 0.98 g/cc to about 1.00 g/cc. Bulk density is an important parameter in the production of nonsegregating compositions, as for example, detergent formulations. Since particle size of sodium dichloroisocyanurate must be kept within a limited range to obtain a flowable product, it has been desired to lower the bulk density of the granular product from that obtained by conventional means to make available an additional parameter in producing non-segregating compositions.

A process has been unexpectedly discovered for producing flowable granular anhydrous sodium dichloroisocyanurate which comprises:

a. compacting, granulating and sizing sodium dichloroisocyanurate dihydrate to obtain a granular dihydrate product at least 60% by weight having a screen size of −10 +70 mesh; and b. drying said granular dihydrate product to produce an ahydrous product having from about zero to about 6% by weight of water, a bulk density of about 0.84 to about 0.94 g/cc and at least 60% by weight having a particle size of −10 +70 mesh.

The sodium dihcloroisocyanurate dihydrate used in the practice of the present invention may be produced by any conventional means, such as the process set forth in U.S. Pat. No. 3,803,144 issued on Apr. 9, 1974 in the name of S. Berkowitz. The dihydrate so produced is a fine powdery material which must first be obtained in the desired granular form. This may be done, for example, by tableting and grinding the dihydrate material. A preferred method of compacting and grinding the dihydrate material involves use of the apparatus schematically shown in the drawing.

Referring to the drawing, the powdered salt is fed into a hopper 10, and by means of feed screws 12 and 14 into the bite between a fixed roll 16 and a compression roll 18, which is forced against the fixed roll 16 by a compression assembly 20. The sheet of salt 22 which results is fed into a granulator 24 which breaks up the sheet into granules and powder; the product is removed at 26.

The roll 18 may be smooth or otherwise designed, as in the form of a sine wave, to produce the particle size desired for the granulated sodium dichloroisocyanurate product. A typical 4 inch sine wave which has about ten complete ⅜ inch sine waves in it, about ¼ inch deep, produces a corrugated sheet which breaks up into mainly −10 +70 mesh product.

The roll 18 is forced against the roll 16 by about 7,500 ±50% pounds of force per linear inch of roll. The granulator 24 may be any device which will break up the continuous sheet which is fed from the roller. Since the sheet is readily friable, a simple hammer mill will work, or a mill with simple rotating shear blades (for example, a Fitz mill).

The granulated sodium dichloroisocyanurate dihydrate is then screened to obtain the desired granular size. It is preferable to obtain granules of the medium (at least 80% by weight of particles having a screen size of −20 +70 mesh) or coarse (at least 80% by weight of particles having a screen size of −10 +70 mesh) size so as to obtain a suitably flowable product.

The sodium dichloroisocyanurate dihydrate in the desired granular form is then dried by an conventional means, as for example, a flash drier or a rotary drier, to produce an ahydrous material containing from about zero to about 6% by weight of water, and preferably from about zero to about 2% by weight of water. Under ambient conditions, temperatures of between 80° and 130° C are preferred. If desired, effective lower or higher temperatures may be utilized, however, under atmospheric conditions, temperatures in excess of about 250° C are not suitable, since the anhydrous product will undergo decomposition at these temperatures. The resulting granular anhydrous product has approximately the same screen size distribution as the hydrated material and a bulk density of from about 6% to about 13% lower than granular sodium dichloroisocyanurate prepared by conventional means. In addition, this granular anhydrous product has a dissolution rate enhanced by about 10% over the product produced by the prior art.

The examples given herein are by way of example only and not by way of limitation. All mesh sizes in the specification and claims are based upon U.S. Standard Screens.

EXAMPLE A (COMPARATIVE EXAMPLE)

"Medium" grade, (at least 80% by weight −20 +70 mesh), anhydrous sodium dichloroisocyanurate granules were produced by the prior art method of sheeting the anhydrous material in a roll compactor into a corrugated, readily frangible sheet which sheet was then fed into the granulator. The product was removed and screened to obtain the desired granular form.

This "medium" grade anhydrous granular product, had a bulk density of about 1.00 g/cc.

EXAMPLE B (COMPARATIVE EXAMPLE)

"Coarse" grade, (at least 80% by weight −10 +70 mesh), anhydrous sodium dichloroisocyanurate granules were produced by the prior art method described above for Comparative Example A. This "coarse" grade anhydrous granular product had a bulk density of about 0.98 g/cc.

EXAMPLE I

"Medium" grade, (at least 80% by weight −20 +70 mesh), sodium dichloroisocyanurate dihydrate granules were obtained by sheeting the hydrated material in a roll compactor into a corrugated, readily frangible sheet which sheet was then fed into the granulator. The product was removed and screened to obtain the desired granular form.

This "medium" grade dihydrate granular product had a bulk density of 1.00 g/cc.

The hydrated product containing about 13.7% water, was then dried in a vacuum oven at a temperature of 100° C until no weight loss was detected. The dried anhydrous granular product was determined to have no more than 1% water.

This "medium" grade anhydrous granular product had the same size distribution as the precursor anhydrous granules and had a bulk density of 0.87 g/cc, which is a 13% reduction over that obtained by the prior art method of Example A.

EXAMPLE II

"Coarse" grade, (at least 80% by weight −10 +70 mesh), sodium dichloroisocyanurate dihydrate granules were prepared by the method described above for Example I.

This "coarse" grade dihydrate product had a bulk density of 1.03 g/cc.

The hydrated product containing about 14% water, was then dried in a vacuum oven at a temperature of 100° C, until no weight loss was detected. The dried anhydrous granular product was determined to have no more than 1% water.

This "coarse" grade anhydrous granular product had the same size distribution as the precursor anhydrous granules and had a bulk density of 0.92 g/cc, which is a 6% reduction over that obtained by the prior art method of Example B.

EXAMPLE III 5 grams of "medium" grade anhydrous sodium dichloroisocyanurate granules, prepared by the prior art method of Example A, were added to 200 ml of distilled water at a temperature of about 25° C, and the mixture was stirred at a fixed rate. Complete dissolution of this material took 113 seconds.

This same procedure, including stirring rate, was followed using "medium" grade anhydrous sodium dichloroisocyanurate granules prepared by the inventive process. Complete dissolution of this material took 100 seconds, which is about 11.5% enhancement over material produced by the prior art method.

EXAMPLE IV

The identical procedure described above for Example III was used to compare the solubility rates of "coarse" grade anhydrous sodium dichloroisocyanurate granules prepared by the prior art method of Example B, and the inventive process, except that the stirrer which was set at the same rate in the composition runs below, was set at a higher rate than in Example III.

The product from the prior art process completely dissolved in 55 seconds whereas that from the inventive process completely dissolved in 50 seconds, which is about a 9% enhancement over material produced by the prior art method.

The invention being thus described, it will be obvious that the same may be varied in many ways. Such variations are not to be regarded as a departure from the spirit and scope of the invention, and all such modifications are intended to be included within the scope of the following claims.

What is claimed is:

1. A process for producing flowable granular anhydrous sodium dichloroisocyanurate which comprises:

a. compacting, granulating and sizing powdered sodium dichloroisocyanurate dihydrate to obtain a granular dihydrate product, at least 60% by weight having a screen size of −10 to +70 mesh; and b. drying said granular dihydrate product to produce an anhydrous product having from about zero to about 6% by weight of water, a bulk density of about 0.84 to about 0.94 g/cc and at least 60% by weight having a particle size of −10 to +70 mesh.

2. Process of claim 1 wherein the granular sodium dichloroisocyanurate dihydrate product is produced by feeding powdered sodium dichloroisocyanurate as hydrated material containing 11 to 14% of water of hydration between two rolls, and one of the rolls is forced against the other with a force of 7,500 ±50% pounds per linear inch, to produce a continuous sheet of sodium dichloroisocyanurate dihydrate which is then broken up into granules and sized.

3. Process of claim 1 wherein the granular dihydrate is sized by screening to obtain a product having at least 80% by weight of particles having a screen size of −20 to +70 mesh.

4. Process of claim 1 wherein the granular dihydrate is sized by screening to obtain a product having at least 80% by weight of particles having a screen size of −10 to +70 mesh.

5. Process of claim 1 wherein the granular dihydrate product is dried to produce an anhydrous product having from about zero to about 2% by weight of water.

6. A granular free-flowing anhydrous sodium dichloroisocyanurate product having a bulk density of from about 0.84 g/cc to about 0.94 g/cc, having at least 60% by weight of particles having a screen size of −10 to +70 mesh and having from about zero to about 6% by weight of water.

7. Product of claim 6 having at least 80% by weight of particles having a screen size of −20 to +70 mesh.

8. Product of claim 6 having at least 80% by wieght of particles having a screen size of −10 to +70 mesh.

9. Product of claim 6 having from about zero to about 2% by weight of water.

* * * * *